United States Patent [19]

Northrup III

[11] Patent Number: 5,593,424
[45] Date of Patent: Jan. 14, 1997

[54] APPARATUS AND METHOD FOR REDUCING AND STABILIZING THE CIRCUMFERENCE OF A VASCULAR STRUCTURE

[75] Inventor: William F. Northrup III, Edina, Minn.

[73] Assignee: Segmed, Inc., Edina, Minn.

[21] Appl. No.: 288,124

[22] Filed: Aug. 10, 1994

[51] Int. Cl.$^6$ ............................................. A61B 17/00
[52] U.S. Cl. ............................ 606/232; 606/1; 606/148; 623/2; 128/898
[58] Field of Search .................................. 606/232, 233, 606/148, 1, 151; 623/2; 128/898

[56] References Cited

U.S. PATENT DOCUMENTS

| | | | |
|---|---|---|---|
| 4,217,665 | 8/1980 | Bex et al. ................................. | 606/157 |
| 4,275,736 | 6/1981 | Chodorow et al. ...................... | 606/233 |
| 4,489,446 | 12/1984 | Reed . | |
| 4,917,698 | 4/1990 | Carpentier et al. . | |
| 5,011,481 | 4/1991 | Myers et al. . | |
| 5,041,130 | 8/1991 | Cosgrove et al. . | |
| 5,061,277 | 10/1991 | Carpentier et al. . | |
| 5,064,431 | 11/1991 | Gilbertson et al. . | |
| 5,104,407 | 4/1992 | Lam et al. . | |
| 5,201,880 | 4/1993 | Wright et al. . | |
| 5,219,359 | 6/1993 | McQuilkin et al. ..................... | 606/232 |
| 5,258,021 | 11/1993 | Duran . | |
| 5,306,301 | 4/1994 | Graf et al. ............................... | 606/151 |
| 5,366,480 | 11/1994 | Corriveau et al. ....................... | 606/232 |
| 5,468,242 | 11/1995 | Reisberg .................................. | 606/151 |

FOREIGN PATENT DOCUMENTS

| | | | |
|---|---|---|---|
| 1335260 | 9/1987 | U.S.S.R. ................................ | 128/898 |

OTHER PUBLICATIONS

Product Pamphlet "Prosthetic Rings and Accessories for Tricuspid and Mitral Valvuloplasty" produced by American Edwards Laboratories, in Dec., 1985.

*Primary Examiner*—Jeffrey A. Schmidt
*Attorney, Agent, or Firm*—Patterson & Keough, P.A.

[57] ABSTRACT

An apparatus and method for reducing the circumference of a vascular structure comprising the steps of providing a plurality of sutures and a plurality of discrete suture support segments of a biocompatible, inert material, each suture support segment having at least two suture holes spaced a predetermined distance (D) apart; individually suturing each discrete suture support segment to the vascular structure with one of the plurality of sutures by effecting a horizontal mattress (U-shaped) suture along the vascular structure through a length of tissue of the vascular structure such that the length (D') of tissue sutured is greater than distance (D); and tightening and tying off the suture, whereby each sutured suture support segment creates an imbrication in the vascular structure, thereby reducing the circumference thereof. A biocompatible, inert stabilizing material may optionally be affixed over the suture support segments and the vascular structure after prior to tying off the suture to stabilize the interval between the suture support segments and eliminate direct exposure of the segmented apparatus to blood.

24 Claims, 3 Drawing Sheets

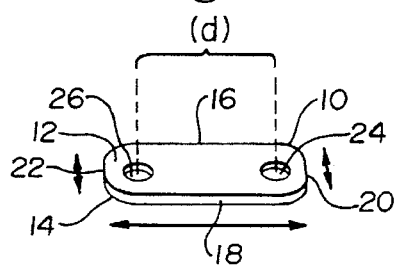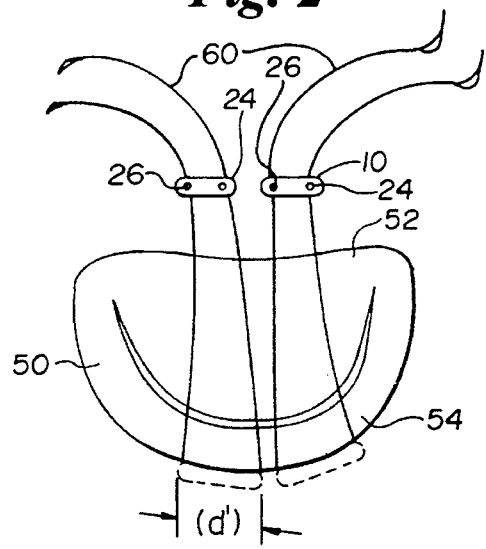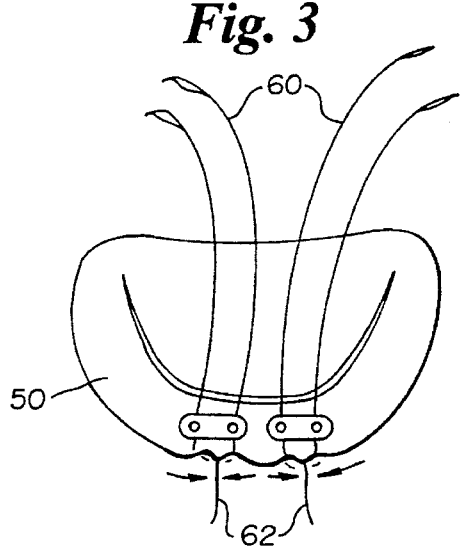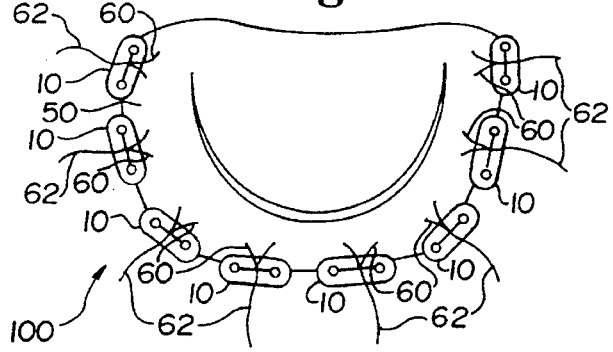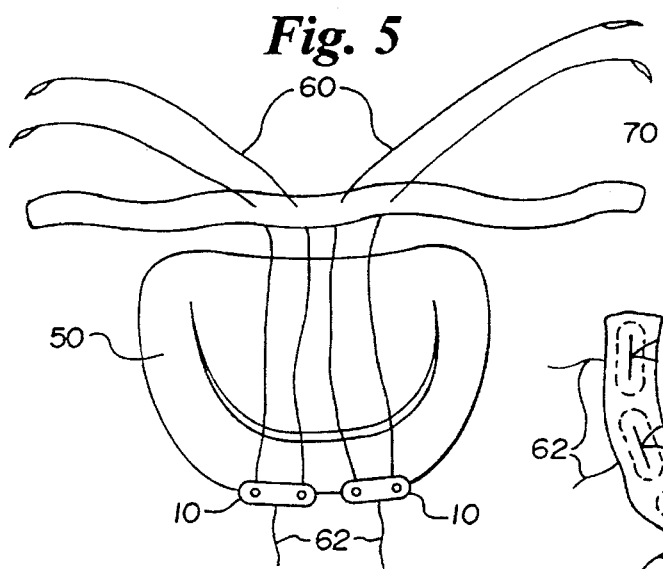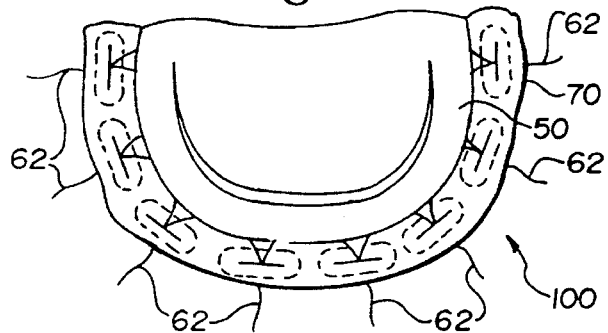

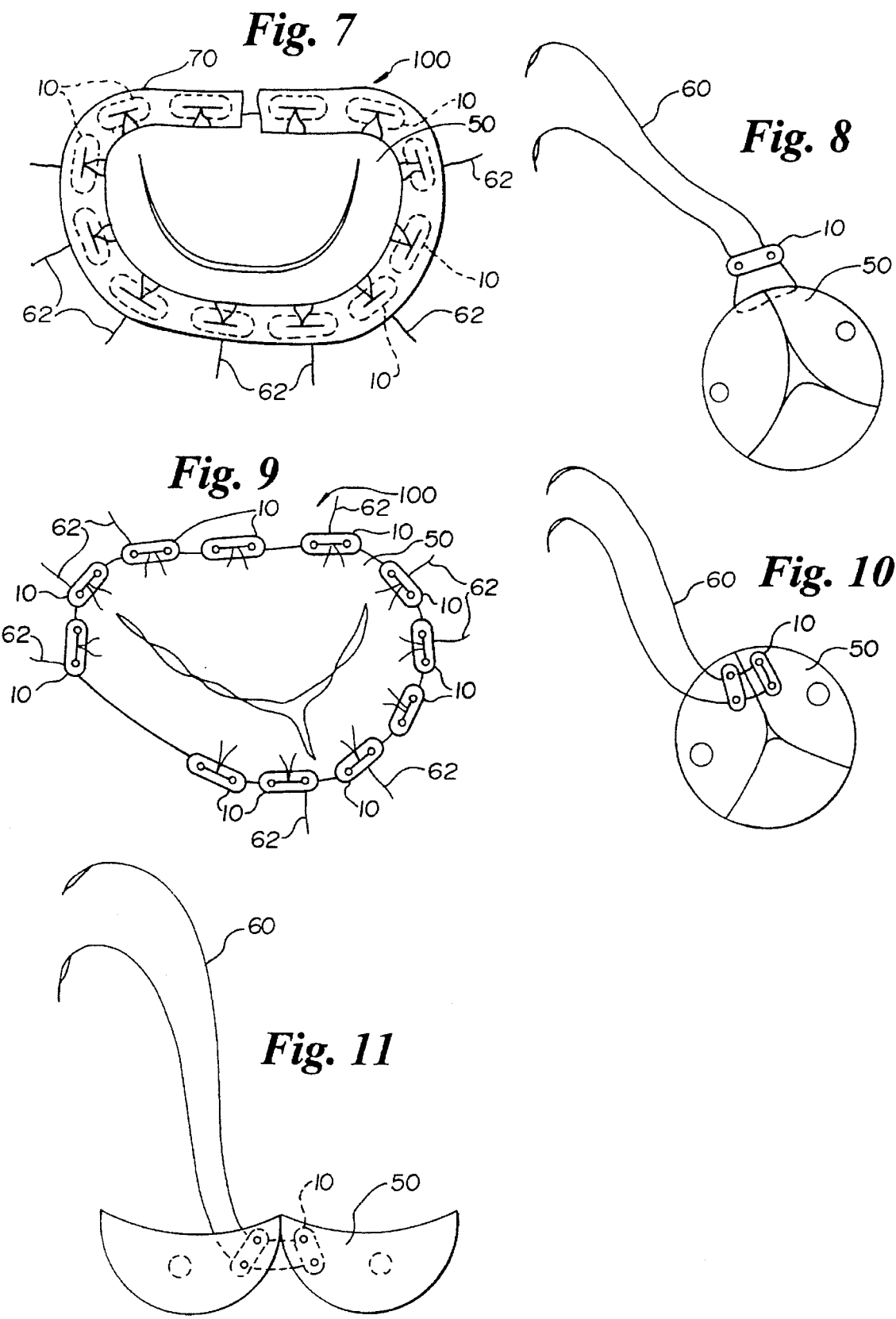

APPARATUS AND METHOD FOR REDUCING AND STABILIZING THE CIRCUMFERENCE OF A VASCULAR STRUCTURE

BACKGROUND OF THE INVENTION

The present invention relates generally to an apparatus and method for reducing the circumference of a vessel, and more particularly to an apparatus and method for reducing the circumference of vascular structures, including cardiac valves.

All artificial or prosthetic heart valves, whether mechanical or bioprosthesis, although greatly improving the condition of the patient, have some serious drawbacks; namely thrombogenicity (tendency towards thrombus formation and subsequent detachment with embolization), and limited durability secondary to tissue structure failure.

Other complications such as noise, interference with hemodynamics, especially in smaller sizes, hemolysis (destruction of blood elements), risk of thromboembolism in all patients who receive mechanical valves, endocarditis (valve infection) and dehiscence of the valve also occur. Because of the risk of embolism, the majority of patients who receive artificial heart valves need to take anticoagulative medication for life with the concomitant risk of hemorrhage and necessary change in life style.

Different and more recent developments in the field of cardiac surgery included attempts to surgically repair diseased vascular tissue, in particular, heart valves. A variety of surgical maneuvers or procedures have been used for this purpose. This type of reconstructive surgery has been shown to be superior to valve replacement in many respects.

Reconstructive surgery, however, is generally more difficult to perform than replacement and is not always possible in every patient. Among the variety of reconstructive maneuvers, valve annuloplasty is the most frequently performed in the tricuspid and mitral valves. Valve annuloplasty is an operation which selectively reduces the size of the valve annulus. For this purpose, a number of prosthetic rings have been developed for the atrioventricular valves. One such well known commercially available ring is the Carpentier (distributed by American Edwards Laboratories) ring.

The Carpentier method of valvuloplasty employing the Carpentier ring is disclosed in the product pamphlet "Prosthetic Rings and Accessories for Tricuspid and Mitral Valvuloplasty", produced by American Edwards Laboratories in December, 1985.

Carpentier et al., U.S. Pat. No. 5,061,277 relates to a flexible cardiac valvular support prosthesis which is generally ring shaped and has a first length which is flexible and a second length which is less flexible than the first length, so the support may shape the annulus while the first length of the support in place in a heart valve annulus allows contraction thereof.

Carpentier et al., U.S. Pat. No. 4,917,698 relates to a multi-segmented annuloplasty ring prosthesis for use in the surgical correction of a deformed heart valve, which provides a substantially circular body comprising in part segments joined together by flexible joints, the body being shaped in proportion to the annulus of a heart valve.

Duran, U.S. Pat. No. 5,258,021 relates to a Sigmoid Valve Annuloplasty Ring in a scalloped shape having three sinusoidal struts to adapt to the anatomical shape of the annulus of the human sigmoid valves. The ring is made of a biocompatible material covered with a biocompatible cloth.

Lam et al., U.S. Pat. No. 5,104,407 relates to a selectively flexible annuloplasty ring for suturing to the annulus of a heart valve, the annular ring comprising a partially flexible length and a partially rigid length. The ring is covered in a suturable material.

Wright et al., U.S. Pat. No. 5,201,880 relates to Mitral and Tricuspid Annuloplasty Rings having a unitary construction with internal drawstrings and a semi-flexible stiffener in the anterior segment.

Cosgrove et al., U.S. Pat. No. 5,041,130 relates to an assembly for holding a substantially flexible lenticular shaped annuloplasty ring in a position for suturing about a valve annulus. The unitary annuloplasty ring contemplated therein is substantially flexible, and is partially circumferential, encompassing only the posterior mitral annulus.

Reed, U.S. Pat. No. 4,489,446 relates to an adjustable heart valve prosthesis with unitary construction including a dynamic stiffener element.

Gilbertson et al., U.S. Pat. No. 5,064,431 relates to an annuloplasty ring of tubular construction including drawstrings selectively adjustable to adjust the annulus to a desired shape.

Myers et al. U.S. Pat. No. 5,011,481 relates to a holder for an annuloplasty ring for use in implantation.

Commercially available annuloplasty rings have several drawbacks. First, they are expensive. Second, unless they are either rigid or sutured to the tissue annulus while still attached to a rigid holder, they may not provide a precise, predictable reproducible annuloplasty because of the unpredictable degree of longitudinal shortening along the circumference of the sutures within the confines of each mattress suture used to secure the ring to the tissue annulus. Each suture is necessarily tied with variable and unpredictable degrees of tension by the operating surgeon.

Third, most mitral rings are completely circumferential committing the operating surgeon to placing sutures in the anterior annulus where dilatation rarely occurs and where a tissue tear from inexact suture placement can produce significant mitral regurgitation. Fourth, a rigid mitral ring, because it is preshaped to an oval configuration, must be precisely placed or an unsatisfactory annuloplasty may result. Fifth, a rigid tricuspid ring can dehisce if not made to conform to the slightly spiral, nonplanar shape of the tissue annulus. Sixth, any rigid ring prevents the normal flexibility of the tissue annulus of the atrioventricular valve during ventricular contraction.

A need exists for an apparatus and method which provides a customized annuloplasty, tailored to the needs of specific pathophysiological situations, including but not limited to a limited annuloplasty or commissuroplasty of any valve annulus, a subtotal annuloplasty of any valve or a complete annuloplasty of any valve annulus. A need also exists for an apparatus and method which allows the repaired vascular structure to retain its flexibility in all planes while preventing further dilatation, or circumferential lengthening of the tissue annulus or vascular structure.

It has been found that to achieve such objects, a commercially available annuloplasty ring is not necessary. Such objects may be effected through use and implantation of an annuloplasty device comprising a series of discrete suture support segments.

SUMMARY OF THE INVENTION

The basic and general object of the present invention is to provide a method and apparatus that maintains the normal shape of a vessel or induces the vessel to regain its normal shape.

More specifically, when performing a valve annuloplasty, the object of the present invention is to implant a device which reduces the circumference of a diseased cardiac valve annulus or vascular structure to the desired size. Specifically, repositioning of displaced and incompetent valvular cusps and commissures or reduction and remodeling of annular or vascular dilatation by precisely defined plications (tucks or folds) at specified points is effected.

The inventive method of reducing the circumference of a vascular structure having an upper portion and a lower portion, said upper and lower portions of the vascular structure defining an upper circumference and a lower circumference of said vascular structure, comprises the steps of:

a) providing a plurality of discrete suture support segments of a biocompatible inert material, each suture support segment further comprising an upper surface, a lower surface, opposite sides, a proximal end, a distal end and at least two suture holes extending from the upper surface to the lower surface thereof and being spaced a predetermined distance (D) apart;

b) providing a suture;

c) individually suturing each suture support segment to the vascular structure whose circumference is to be reduced by means of a horizontal mattress (U-shaped) suture along the vascular structure through a length of tissue of the vascular structure such that the length (D') of tissue sutured is greater than distance (D); and d) tightening and tying off the suture, whereby each sutured segment creates an imbrication in the vascular structure, thereby reducing the circumference thereof by an amount equal to (D')–(D).

Alternatively, the method may comprise the further step of affixing a biocompatible, inert stabilizing material over the suture support segments and the vascular structure by means of horizontal mattress sutures through each suture support segment and through the tissue of the vascular structure, said stabilizing material being of predetermined dimensions sufficient to cover the suture support segments affixed to the vascular structure, thereby stabilizing the interval between the suture support segments in order to prevent further lengthening of the vascular structure, and eliminating direct exposure of the suture support segments to blood.

BRIEF DESCRIPTION OF THE FIGURES

FIG. 1 is a perspective view of a suture support segment of the present invention;

FIG. 2 shows a top view of a vascular structure (i.e., mitral valve) upon which suture support segments for reducing the circumference of a vascular structure according to the present invention are being sutured;

FIG. 3 shows a top view as in FIG. 1 wherein the tissue of the vascular structure has been imbricated according to the present invention;

FIG. 4 is a top view as in FIG. 1 showing the suture support segments in place on a vascular structure (i.e., mitral valve) whose circumference is thereby reduced according to the present invention;

FIG. 5 is a top view as in FIG. 1 showing optional fixation of the stabilizing material over the suture support segments;

FIG. 6 is a top view as in FIG. 1 showing the suture support segments and stabilizing material in place;

FIG. 7 is a top view of a complete mitral valve annuloplasty according to the present invention;

FIG. 8 is a top view of an aortic valve commissuroplasty (localized annuloplasty) according to the present invention;

FIG. 9 is a top view of a tricuspid valve annuloplasty according to the present invention;

FIGS. 10 is a top view of a commissural annuloplasty of a semilunar valve;

FIG. 11 is a side view of a commissural annuloplasty of a semilunar valve;

DETAILED DESCRIPTION OF THE INVENTION

Figure 12:
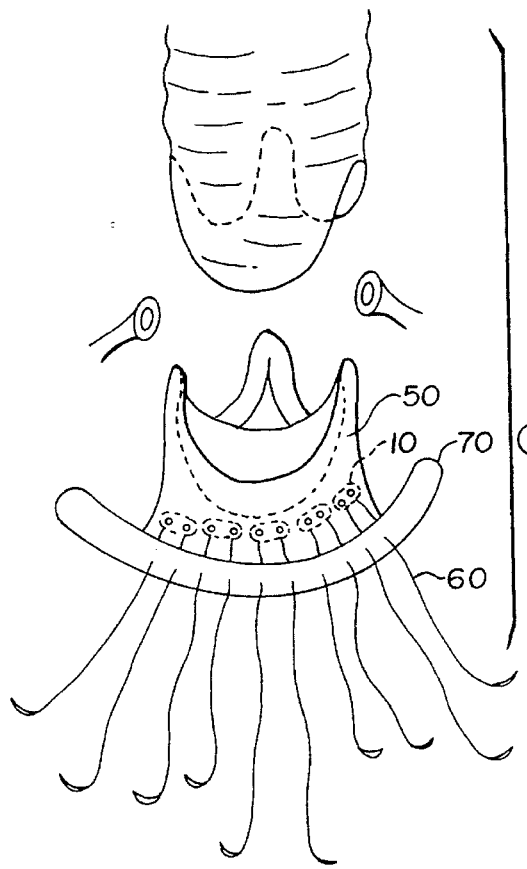
FIGS. 12 and 13 are views of a stabilizing annuloplasty of the aortic valve annulus in an aortic valve-sparing root replacement with a dacron conduit, FIG. 12 being a side view of stabilization from the outside of the reconstructed aortic root and FIG. 13 being a view of an opened aorta showing the stabilization from the inside of the reconstructed aortic root.

While this invention may be embodied in many different forms, there are described in detail herein specific preferred embodiments of the invention. This description is an exemplification of the principles of the invention and is not intended to limit the invention to the particular embodiments illustrated.

The present invention provides an apparatus and method for reducing the circumference of a vascular structure. The present invention also provides an apparatus and method for permanently reconstructing a vascular structure to a normal configuration, to restore its original form and function. The apparatus comprises a plurality of suture support segments like that shown generally at 10 in FIG. 1, sutured to a vascular structure. A plurality of suture support segments is shown in place generally at 100 in FIG. 4. As shown in FIG. 1, each individual suture support segment 10 comprises an upper surface 12, a lower surface 14, opposite sides 16, 18, a proximal end 20, and a distal end 22. Each suture support segment 10 has exactly two suture holes. The embodiment shown at FIG. 1 has a first suture hole 24 and a second suture hole 26 extending from upper surface 12 to lower surface 14, spaced a predetermined distance (D) apart. Suture holes 24, 26 should be large enough to accommodate a 2-0 suture and swedged-on needle. In addition, suture holes 24, 26 should be smooth in order to prevent suture fraying or cutting when suture 60 is tied. The distance (D) between suture holes 24, 26 may be varied, although an interval of 5 mm (±3 mm) from center to center of holes 24, 26 is suitable.

Although any suitable suture may be used, the most preferred as shown in the figures has a swedged-on surgical needle at each end thereof. Alternatively, a single needle suture may be used.

Suture support segment 10 may be made of any suitable material which is biocompatible with blood and tissue, inert, non-corrosive and non-thrombogenic. As a practical matter, the material of which suture support segment 10 is made should be a substance already approved for intra-vascular use by the FDA such as titanium. Suture support segment 10 must be rigid or semi-rigid in the longitudinal dimension, and must not be deformable, so that it does not buckle when suture 60 is tied.

Although suture support segment 10 may be of any suitable shape, the spatulated shape shown in FIG. 1 is quite effective. The minimum dimension from outside edge of suture hole to the end of suture support segment 10 in order to minimize the chance of abutment or overlap of adjacent suture support segments is about 1 mm. The minimum width to minimize mass but not to allow cutting into tissue is between about 2 mm–4 mm. The minimum thickness to reduce mass but avoid buckling of suture support segment 10 is about 1 mm.

The method of reducing the circumference of vascular structure is shown at FIGS. 2–6. As shown at FIG. 2, vascular structure 50 has an upper portion 52 and a lower portion 54, said upper and lower portions 52, 54 defining an upper circumference and a lower circumference of vascular structure 50.

Apparatus 100 comprising a plurality of suture support segments 10. Suture support segments 10 are individually affixed to vascular structure 50 whose circumference is to be reduced, by means of a horizontal mattress (U-shaped) suture 60 along vascular structure 50 through a length of tissue of vascular structure 50. Referring to FIG. 2, the suture 60 traverses a longer distance along vascular structure 50 than the distance (D) between suture holes 24, 26 of suture support segment 10. Specifically, the length or distance (D') between the entry and exit of suture 60 is greater than distance (D) between suture holes 24, 26 of suture support segment 10. As shown in FIGS. 2 and 3, both ends of suture 60 are brought up through suture holes 24, 26 of suture support segment 10. The length (D') of tissue of vascular structure 50 sutured is greater than distance (D), whereby each sutured segment 10 creates an imbrication, or tuck 62, in vascular structure 50, thereby reducing the circumference thereof.

Sutures 60, when tied, will reduce the circumference of a vascular structure by an amount equal to (D')–(D), the difference between the length (D') each individual mattress suture 60 travels in the tissue of vascular structure 50 and the distance (D) between the 2 suture holes 24, 26 in the individual suture support segment 10. In other words, vascular structure 50 is imbricated underneath suture support segment 10, within the individual mattress suture, by a precise amount depending on the linear distance (D') along the tissue of vascular structure 50 which the individual suture 60 travels.

A plurality of suture support segments 10 in place is shown at FIG. 4.

Referring to FIG. 5, a biocompatible, inert stabilizing material 70 may optionally be provided. As shown, stabilizing material 70 is also affixed over the segmented apparatus and the vascular structure by means of horizontal mattress sutures 60 through each segment and through the tissue of vascular structure 50. Stabilizing material 70 may be affixed to vascular structure 50 by means of the same sutures 60 used to affix segments 10 thereto. Both ends of suture 60 are brought up through stabilizing material 70 prior to tying of suture 60.

Alternatively, the stabilizing material and suture support segment may be sutured to vascular structure 50 with one continuous suture using a single needle. The mattress suture would be effected by passing the needle and suture first through the stabilizing material from an entry point in the upper surface thereof through the lower surface thereof, then through a suture hole in the suture support segment, suturing the length of tissue of the vascular structure, passing the suture through a second suture hole in the suture support segment, passing the suture through the stabilizing material from the lower surface thereof and out an exit point in the upper surface thereof. The suture would then be tightened and tied off such that the suture knot formed would sit on the upper surface of the stabilizing material. Alternatively, a running mattress suture would be possible by tying a single suture to itself or to an additional suture or by repeating the course of the running mattress suture in reverse.

Stabilizing material 70 is of predetermined dimensions sufficient to cover apparatus 100 affixed to vascular structure 50, and may actually be another layer of tissue such as autologous, homologous or heterologous pericardium, or alternatively may be made of any suitable fabric, such as dacron.

Stabilizing material 70, shown in place in FIG. 6, stabilizes the interval between sutures 60, preventing further dilatation or circumferential lengthening of the tissue annulus or vascular structure between sutures. The stabilizing material 70 also eliminates direct exposure of the segmented apparatus 100 to blood.

The practice of the present invention achieves several objectives and advantages. The objectives and advantages are as follows.

The segmented apparatus of the present invention is much less expensive to produce than commercial annuloplasty rings, as it comprises discrete suture support segments which are economical to produce.

The apparatus and method allows precise imbrication within each mattress suture supported by suture support segments. This is not possible with any annuloplasty device which is deformable in a longitudinal direction unless the device is attached to a rigid holder while the sutures are tied. The present apparatus and method allows for an absolutely precise, predictable and reproducible annuloplasty.

Figure 13:
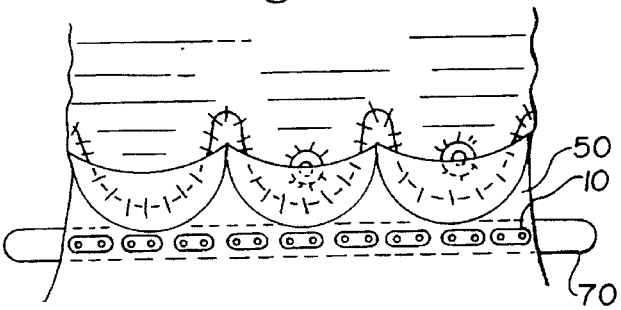
Figure 14:
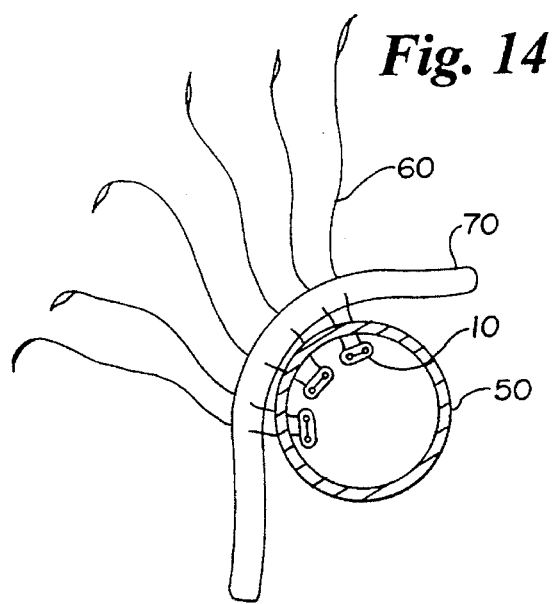
FIG. 14 is a top sectional cut-away view of a left ventricular outflow tract showing the level of the stabilizing annuloplasty immediately below the aortic valve (as shown in FIGS. 12 and 13).

The inventive apparatus and method provide construction of a customized annuloplasty, not possible with commercial annuloplasty rings. A limited annuloplasty or commissuroplasty of any valve annulus, as shown in FIGS. 8, 10 and 11 can be performed, as can a posterior mitral valve annuloplasty as shown in FIGS. 4 and 6, as well as a subtotal annuloplasty of any valve such as the tricuspid valve, as shown in FIG. 9, or a complete annuloplasty of any valve annulus as shown in FIG. 7. FIGS. 10 and 11 show a commissural annuloplasty of a semilunar valve. FIGS. 12, 13 and 14 show a stabilizing annuloplasty of the aortic valve annulus.

The discrete suture support segments allow flexibility of the annulus or vascular structure in all planes, analogous in principle to a chain-link fence, although the links are separate. The resulting annuloplasty is more physiologic than with a rigid ring since it is flexible in all planes. In the case of the mitral and tricuspid valve annulus, systolic contraction is still possible.

The present invention provides not only an annuloplasty device which is not only less expensive than commercially available annuloplasty rings, but also a more precise, predictable reproducible annuloplasty than is provided by any flexible ring not attached to a rigid holder while the sutures are tied. The discrete suture support segments make it possible to reduce the circumference of the valve annulus by a specific length. A customized annuloplasty, including but not limited to a limited annuloplasty or commissuroplasty of any valve annulus, a subtotal annuloplasty of any valve or a complete annuloplasty of any valve annulus may thereby be provided.

Repair of a vascular structure with the present apparatus and method allows the repaired vascular structure to retain its flexibility in all planes, and further minimizes the possibility of dehiscence of the vascular structure, and the possibility of further dilatation, or circumferential lengthening of the vascular structure. Further, the possibility of failure of the present apparatus when in place at the tissue annulus is lessened by providing discrete suture support segments. Conversely, a rigid, unitary annuloplasty ring when implanted will by definition resist any physiological motion of the tissue annulus either downward (away from the lower surface of the ring) or inward (toward the orifice of the ring), and may therefore come out of its implanted site.

In addition, the need for temporary anticoagulation recommended with commercial annuloplasty rings is probably unnecessary with the present invention, especially if the segmented apparatus is covered with a stabilizing material such as pericardium, as no thrombogenic surfaces are exposed to the blood except for suture knots.

Suture knots are less likely to come untied when used in conjunction with a stabilizing material which is significantly deformable in a longitudinal direction, such as pericardium, since individual sutures can be tied firmly with uniform maximal tension against the non-deformable suture support segment without any possibility of additional longitudinal shortening of the tissue annulus due to excessive tension during knot-tying.

When the apparatus and method of the present invention is used in infants and growing children without the stabilizing material, the potential for growth of a vascular structure or cardiac valve annulus between the suture support segments is retained.

When used to perform a commissural annuloplasty of a semilunar valve, as shown in FIGS. 10 and 11, and the suture support segments are vertically oriented within the sinus on either side of the commissure just short of the leaflet hinge, no reduction in leaflet height occurs when the suture is tied. Such leaflet height reduction at the commissures could occur if the buttressing material were deformable (e.g. teflon felt pledget).

A "stabilizing" annuloplasty of the aortic valve annulus could be accomplished in operations wherein a dilated aortic root is replaced with a dacron conduit and the aortic valve is spared (e.g., Yacoub and David) particularly if the conduit is used to create "pseudo-sinuses" and does not engage the actual aortic valve annulus with sutures (FIGS. 12, 13). In such cases the suture support segments could be placed on the endocardial surface of the left ventricular outflow tract in a single horizontal plane immediately below the lowest points of the scalloped aortic valve sinuses avoiding contact with the leaflet hinge. The stabilizing material could then be placed on the epicardial surface (FIG. 14).

Although the present invention is particularly suited for reducing the circumference of vascular structures such as cardiac valves as indicated hereinabove, the apparatus and method may be applied to reduce the circumference of any valve, vessel or lumen in the body, including those in the digestive, genito-urinary, circulatory or respiratory systems. By the method described hereinabove, a plurality of suture support segments are sutured around a predetermined portion of the circumference of the structure, for example an intestinal lumen.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A method of reducing the circumference of a vascular structure having an upper portion and a lower portion, said upper and lower portions of the vascular structure defining an upper circumference and a lower circumference of said vascular structure, said method comprising the steps of:
   a) providing a plurality of discrete suture support segments of a non-deformable biocompatible inert material, each suture support segment further comprising an upper surface, a lower surface, opposite sides, a proximal end, a distal end and two suture holes extending from the upper surface to the lower surface thereof and being spaced a predetermined distance (D) apart, each suture support segment further being rigid or semi-rigid in a longitudinal dimension defined by said opposite sides;
   b) providing a plurality of sutures with a first end and a second end and at least one surgical needle attached to an end thereof;
   c) individually suturing each said suture support segment to the vascular structure whose circumference is to be reduced by using one of the plurality of sutures to effect a horizontal mattress (U-shaped) suture along a length of tissue of the vascular structure defined by an entry point and an exit point of said suture in the vascular structure such that the length (D') of tissue sutured is greater than distance (D);
   d) tightening the mattress suture; and
   e) tying off the suture such that a suture knot is formed which sits on the upper surface of the suture support segment between two suture holes, whereby each sutured suture support segment creates an imbrication in the vascular structure thereby reducing the circumference thereof by an amount corresponding to (D')–(D).

2. The method of claim 1 further comprising suturing at least one suture support segment to the lower portion of the vascular structure, whereby the lower circumference of the vascular structure is reduced.

3. The method of claim 1 wherein the step of providing a plurality of suture support segments comprises providing suture support segments having a first suture hole near the proximal end of the suture support segment and a second suture hole near the distal end of the suture support segment, said first and second suture holes being spaced a predetermined distance apart.

4. The method of claim 1 wherein the step of providing a plurality of suture support segments comprises providing suture support segments having smooth suture holes of a diameter which accommodates a 2-0 suture and a swedged-on suture needle.

5. The method of claim 1 wherein the step of providing a plurality of suture support segments comprises providing suture support segments having a length of about 5 mm and a width of about 2–4 mm.

6. The method of claim 5 wherein the step of providing suture support segments comprises providing suture support segments having a thickness of at least about 1 mm.

7. The method of claim 1 wherein the step of providing a plurality of suture support segments comprises providing suture support segments having a spatulated shape.

8. The method of claim 1 wherein the step of suturing to a vascular structure comprises suturing to a cardiac valve annulus.

9. The method of claim 1 wherein the step of suturing to a vascular structure comprises suturing to a mitral valve.

10. The method of claim 1 wherein the step of suturing to a vascular structure comprises suturing to a tricuspid valve.

11. The method of claim 1 wherein the step of suturing to a vascular structure comprises suturing to an aortic valve.

12. The method of claim 1 wherein the step of suturing to a vascular structure comprises suturing to a pulmonic valve.

13. The method of claim 1 wherein the step of providing suture support segments comprises providing suture support segments made of titanium.

14. A method of reducing the circumference of a vascular structure having an upper portion and a lower portion, said upper and lower portions of the vascular structure defining an upper circumference and a lower circumference of said vascular structure, said method comprising the steps of:

(a) providing a plurality of discrete suture support segments of a biocompatible inert material, each suture support segment further comprising an upper surface, a lower surface, opposite sides, a proximal end, a distal end and at least two suture holes extending from the upper surface to the lower surface thereof and being spaced a predetermined distance (D) apart;

(b) providing a plurality of sutures with a first end and a second end and at least one surgical needle attached to an end thereof;

(c) individually suturing each said suture support segment to the vascular structure whose circumference is to be reduced by using one of the plurality of sutures to effect a horizontal mattress (U-shaped) suture along a length of tissue of the vascular structure defined by an entry point and an exit point of said suture in the vascular structure such that the length (D') of tissue sutured is greater than distance (D);

(d) tightening the mattress suture;

(e) tying off the suture such that a suture knot is formed which sits on the upper surface of the suture support segment between two suture holes, whereby each sutured suture support segment creates an imbrication in the vascular structure thereby reducing the circumference thereof by an amount corresponding to (D')–(D);

(f) providing a biocompatible, inert stabilizing material of predetermined dimensions sufficient to cover the suture support segments sutured to the vascular structure, said stabilizing material having an upper surface and a lower surface;

(g) securing the stabilizing material over the plurality of suture support segments and the vascular structure, whereby the interval between the sutured suture support segments is stabilized and direct exposure of the sutured suture support segments to blood is eliminated.

15. The method of claim 14 wherein the stabilizing material is secured over the plurality of suture support segments and the vascular structure by suturing the stabilizing material over the suture support segments and the vascular structure after tightening the suture but prior to tying the suture off.

16. The method of claim 14 wherein the mattress suture is performed comprising the following steps:

a) passing the suture through the stabilizing material from an entry point in the upper surface thereof through the lower surface thereof;

b) passing the suture through a suture hole in the suture support segment;

c) suturing the length of tissue of the vascular structure between the entry and exit points;

d) passing the suture through a second suture hole in the suture support segment;

e) passing the suture through the stabilizing material from the lower surface thereof and out an exit point in the upper surface thereof;

f) tightening the mattress suture; and g) tying off the suture such that a suture knot is formed which sits on the upper surface of the stabilizing material.

17. The method of claim 14 wherein the step of providing a stabilizing material comprises providing a stabilizing material made of fabric.

18. The method of claim 17 wherein the step of providing a stabilizing material made of fabric comprises providing a stabilizing material made of dacron.

19. The method of claim 14 wherein the step of providing a stabilizing material comprises providing a layer of tissue.

20. The method of claim 19 wherein the step of providing a stabilizing material comprises providing a layer of autologous, homologous or heterologous pericardium, whether untreated or treated with a tanning agent such as glutaraldehyde or cryopreserved.

21. The method of claim 14 wherein the step of providing suture support segments comprises providing suture support segments made of titanium.

22. A method of reducing the circumference of a vascular structure having an upper portion and a lower portion, said upper and lower portions of the vascular structure defining an upper circumference and a lower circumference of said vascular structure, said method comprising the steps of:

(a) providing a plurality of discrete suture support segments of a biocompatible inert material, each suture support segment further comprising an upper surface, a lower surface, opposite sides, a proximal end, a distal end and at least two suture holes extending from the upper surface to the lower surface thereof and being spaced a predetermined distance (D) apart;

(b) providing a plurality of sutures with a first end and a second end and at least one surgical needle attached to an end thereof;

(c) individually suturing each said suture support segment to the vascular structure whose circumference is to be reduced by using one of the plurality of sutures to effect a horizontal mattress (U-shaped) suture along a length of tissue of the vascular structure defined by an entry point and an exit point of said suture in the vascular structure such that the length (D') of tissue sutured is greater than distance (D);

(d) tightening the mattress suture;

(e) tying off the suture such that a suture knot is formed which sits on the upper surface of the suture support segment between two suture holes;

(f) suturing a plurality of suture support segments around the upper circumference of the vascular structure;

(g) suturing a plurality of suture support segments around the lower circumference of the vascular structure;

whereby each sutured suture support segment creates an imbrication in the vascular structure which reduces the circumference thereof by an amount corresponding to (D')–(D) for each suture support segment sutured to the vascular structure, and the entire circumference of the vascular structure is reduced.

23. A method of reducing the circumference of an anatomical structure, said method comprising the steps of:

a) providing a plurality of discrete suture support segments of a non-deformable biocompatible inert material, each suture support segment further comprising an upper surface, a lower surface, opposite sides, a proximal end, a distal end and two suture holes extending from the upper surface to the lower surface thereof and being spaced a predetermined distance (D) apart, said suture support segments being rigid or semi-rigid in a longitudinal dimension defined by said opposite sides;

b) providing a plurality of sutures;

c) individually suturing each said suture support segment to the anatomical structure whose circumference is to be reduced by using one of the plurality of sutures to effect a horizontal mattress (U-shaped) suture along a length of tissue of the anatomical structure defined by an entry and an exit of said suture such that the length (D') of tissue sutured is greater than distance (D); and d) tightening and tying off the suture such that a suture knot is formed which sits on the upper surface of the suture support segment between two suture holes, whereby each sutured suture support segment creates an imbrication in the anatomical structure thereby reducing the circumference thereof by an amount corresponding to (D')–(D).

24. The method of claim 23 wherein the step of providing suture support segments comprises providing suture support segments made of titanium.

* * * * *